US008778389B2

(12) United States Patent
Carminati et al.

(10) Patent No.: US 8,778,389 B2
(45) Date of Patent: *Jul. 15, 2014

(54) MEDICAMENT FOR THE TREATMENT OF FUNGAL INFECTIONS PARTICULARLY ASPERGILLOSIS

(75) Inventors: Paolo Carminati, Milan (IT); Giovanni Salvatori, Rome (IT); Romani Luigina, Perugla (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 1315 days.

This patent is subject to a terminal disclaimer.

(21) Appl. No.: 11/579,805

(22) PCT Filed: Apr. 28, 2005

(86) PCT No.: PCT/IT2005/000247
§ 371 (c)(1),
(2), (4) Date: Nov. 7, 2006

(87) PCT Pub. No.: WO2005/107791
PCT Pub. Date: Nov. 17, 2005

(65) Prior Publication Data
US 2008/0026997 A1    Jan. 31, 2008

(30) Foreign Application Priority Data
May 7, 2004   (IT) .............................. RM2004A0223

(51) Int. Cl.
*A61K 9/127*   (2006.01)
(52) U.S. Cl.
USPC ....................................................... 424/450
(58) Field of Classification Search
USPC ........................................................ 424/450
See application file for complete search history.

(56) References Cited

U.S. PATENT DOCUMENTS

| | | | |
|---|---|---|---|
| 5,059,591 A * | 10/1991 | Janoff et al. .................... 514/31 |
| 5,965,156 A * | 10/1999 | Proffitt et al. ................. 424/450 |
| 7,683,032 B2 | 3/2010 | Carminati et al. | |
| 2005/0187161 A1* | 8/2005 | Kontoyiannis et al. ......... 514/14 |
| 2005/0215648 A1* | 9/2005 | Li et al. ......................... 514/690 |
| 2009/0275508 A1 | 11/2009 | Romani et al. | |
| 2009/0286726 A1 | 11/2009 | Carminati et al. | |
| 2010/0209442 A1 | 8/2010 | Carminati et al. | |

FOREIGN PATENT DOCUMENTS

| WO | 99/32516 | * | 7/1999 |
|---|---|---|---|
| WO | 99/32516 A | | 7/1999 |

OTHER PUBLICATIONS

Garlanda et al in Nature (London), vol. 420, No. 6912, Nov. 14, 2002, pp. 182-186.*
Hopfer et al in Antimicrobial agents and chemotherapy, Dec. 1987, vol. 31, No. 12, pp. 1978-1981.*
International Search Report of PCT/IT2005/000247 mailed Aug. 10, 2005.
Garlanda Cecilia et al: "Non-redundant role of the long pentraxin PTX3 in anti-fungal innate immune response" Nature (London), vol. 420, No. 6912, Nov. 14, 2002, pp. 182-186, XP002337598 ISSN: 0028-0836 cited in the application the whole document.
Patterson Thomas F et al: "Invasive aspergillosis: Disease spectrum, treatment practices, and outcomes" Medicine (Baltimore), vol. 79 No. 4, Jul. 2000, pp. 250-260, Xp009051005, ISSN:0025-7974 cited in the application the whole document.
Gaziano Roberta et al: "Anti-*Aspergillus fumigatus* efficacy of pentraxin 3 alone and in combination with antifungals" Antimicrobial Agents and Chemotherapy, vol. 48, No. 11, Nov. 2004, pp. 4414-4421, XP002337599 ISSN: 0066-4804 cited in the application the whole document.

* cited by examiner

*Primary Examiner* — Gollamudi Kishore
(74) *Attorney, Agent, or Firm* — Lucas & Mercanti, LLP

(57) ABSTRACT

The combination of pentraxin PTX3 with antifungal agents is described for the treatment of fungal infections and particularly for infections caused by *Aspergillus fumigatus*. Thanks to the synergistic effect of the two drugs, the combination allows the administration of suboptimal doses of antifungal agent.

1 Claim, 7 Drawing Sheets

Figure 1:
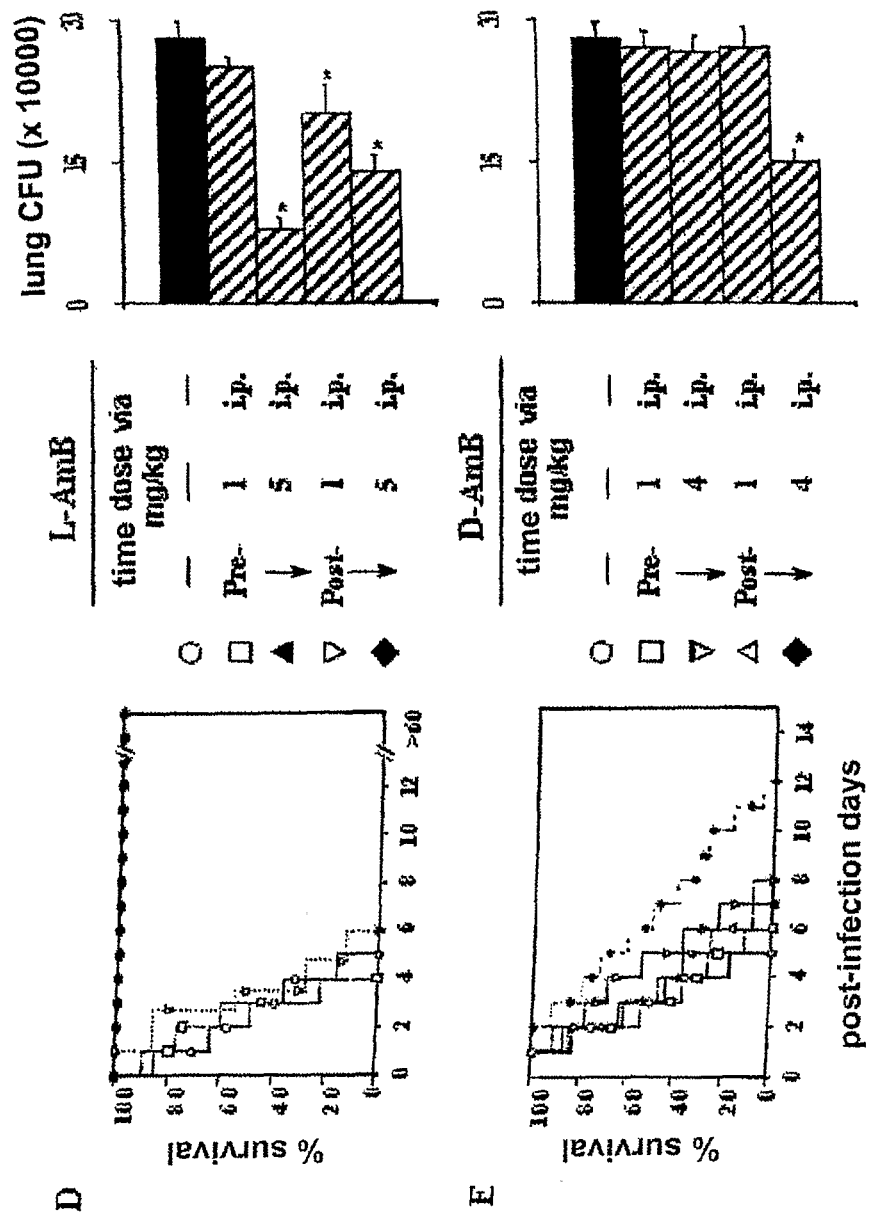

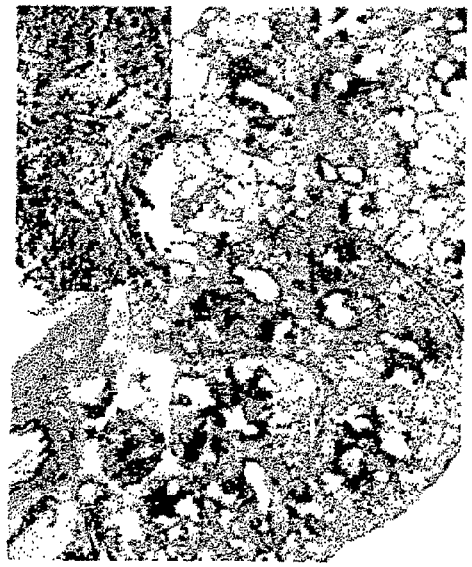
FIG. 3

MEDICAMENT FOR THE TREATMENT OF FUNGAL INFECTIONS PARTICULARLY ASPERGILLOSIS

This application is the US national phase of international application PCT/IT2005/000247, filed 28 Apr. 2005, which designated the U.S. and claims priority of IT RM2004A000223, filed 7 May 2004, the entire contents of each of which are hereby incorporated by reference.

The present invention relates to a medicament consisting of a combination of pentraxin PTX3 and an antifungal for the treatment of aspergillosis.

BACKGROUND TO THE INVENTION

Invasive aspergilosis (IA) is the main cause of nosocomial pneumonia and of death in allogeneic bone marrow (BM) transplants with an infection rate estimated as ranging from 8% to 15% and an associated mortality rate of approximately 90% (3, 16, 30, 36, 47). Despite progress in early diagnosis and therapy with the new anti-fungal agents (6, 31), the majority of cases of AI remain undiagnosed and untreated (16). The most important risk factor for AI historically used to be neutropaenia. However, the advances made in the preparation of patients undergoing chemotherapy and transplantation have led to a significant reduction in the neutropaenia period. Numerous studies have documented that aspergillosis manifests itself following bone marrow transplants concomitantly with the onset of graft-versus-host (GvH) disease (30). The occurrence of IA also in non-neutropaenic patients (17) confirms the importance of specific defects in both the innate and adaptive immune effector mechanisms in the pathogenesis of the disease (13, 20, 22, 32, 39, 43, 44). In particular, the role of Th lymphocytes in providing an essential secondary defence against the fungus has recently been assessed (8-10, 12, 14, 23, 26). Since IA is extremely rare in immunocompetent individuals, therapy aimed at enhancing the host's immune response offers a new and promising approach in the treatment of this infection.

The innate immune system has evolved in a complex, multi-faceted manner to protect lung tissue against infections. The protection of lung tissue is thought to comprise not only a preventive control of microbial proliferation, but also the execution of a balanced inflammatory response sufficient to contain the infection without inducing dangerous degrees of alveolar exudation and infiltration. The molecular components of the alveolar lining have recently been the focus of considerable attention as primary immunomodulators in infections (28, 29).

The pentraxins (PTX) are a superfamily of proteins conserved during the evolution from *Limulus polyphemus* to man, generally characterised by a pentameric structure (21). PTX3 is a prototype of the long pentraxin that consists in an N-terminal portion coupled to the pentraxin C-terminal domain, the latter being a homologue of the short PTXs (7). PTX3 is secreted by various types of cells, particularly by mononuclear phagocytes, endothelial cells and dendritic cells (DC), in response to the primary inflammatory cytokines in vitro and in vivo (11, 38, 18). Increases in circulating levels of this protein have been detected in various different infectious and inflammatory conditions (37, 19, 34, 41). PTX3 binds a number of selected microbial agents (e.g. *A. fumigatus* conidia and *P. aeruginosa*) and activates various effector pathways of the immune system to combat the infectivity of the pathogen (20). Analysis of PTX3-deficient mice has demonstrated that PTX3 is a pattern recognition receptor (PRR) that plays a non-redundant role in the resistance to selected pathogens (20). The susceptibility of PTX3-deficient mice to *A. fumigatus* has been associated with unsuccessful organisation of the type I adaptive immune response, but is restored by the exogenous administration of recombinant PTX3 (20).

There is a need for therapeutic advances in combating aspergillosis, despite the recent expansion of the antifungal armamentarium (45).

Researchers are beginning to explore new strategies with a singular combination of antifungals and cytokines (46). Treatment with amphotericin B, a first-choice drug, is limited by dose-related nephrotoxicity which precludes full-dose therapy in patients who have been submitted to BM transplants (24). Various amphotericin B lipid-based formulations have been developed to reduce the toxicity associated with conventional D-AmB (25), as well as with L-AmB (2). The pharmacokinetic profile of L-AmB toxicity is more favourable than that of D-AmB, thus making full-dose therapy possible. Nevertheless, the failure rate is still a matter for concern (1). Published murine models of IA, in which the efficacy of antifungal agents has been assessed, have relied on neutropaenia induced by chemotherapy with or without corticosteroids to make the mice less susceptible to infection. Recently there has been an increase in the development of new antifungal agents for the treatment of IA, with drug classes characterised by new therapeutic targets (45), which are giving rise to new expectations for the treatment of IA and which increase the number of new combined therapies possible (45). On the basis of the treatment of other infectious diseases (4), combination therapy would appear to be an important therapeutic option.

SUMMARY OF THE INVENTION

It has now been found that pentraxin PTX3 exerts a surprising synergistic effect when combined with other antifungal agents, thus permitting the preparation of a drug characterised by suboptimal doses of antifungal. This characteristic proves to be advantageous in terms of the greater manageability of the medicament, in that it is capable of substantially limiting the side effects characteristic of its individual active ingredients.

Therefore, one object of the present invention is a combination of pentraxin PTX3 and an antifungal agent, as well as a pharmaceutical composition containing it and the use of said combination for the preparation of a medicament for the prophylactic or therapeutic treatment of fungal infections, particularly aspergillosis.

DETAILED DESCRIPTION OF THE INVENTION

Pentraxin PTX3 and its various therapeutic uses are described in various patent applications filed in the name of the present applicant.

International patent application WO 99/32516 describes the sequence of the protein and its use in infectious, inflammatory or tumoral diseases. Other uses of the long pentraxin PTX3 are described in WO02/38169, WO 02/36151, WO 03/011326, and WO 03/084561.

In a preferred embodiment of the invention, the antifungal agent is amphotericin B, more preferably in the deoxycholate form known on the market under the trade mark Fungizone (Bristol-Myers Squibb) or in the liposomal formulation known on the market under the trade mark AmBisome (GILEAD).

As regards the aspects relating to the industrial applicability of the present invention, the long pentraxin PTX3 and the antifungal will be in the form of a pharmaceutical composition in which the active ingredients are solubilised and/or vehicled by pharmaceutically acceptable excipients and/or diluents.

Examples of pharmaceutical compositions that can be used for long pentraxin PTX3 are also those described in WO 99/32516.

The combination according to the present invention can be administered by the enteral or parenteral routes.

The daily dose will depend, according to the judgement of the primary care physician, on the weight, age and general condition of the patient.

It is pointed out that the preparation of said pharmaceutical compositions, including the slow-release ones, can be accomplished using common techniques and instrumentation well known to pharmacists and to experts in pharmaceutical technology.

In a particular embodiment of the invention, the fungal infection is invasive aspergillosis (IA).

The combination according to the invention has been assessed in the murine bone marrow transplant model which replicates the immunodeficiency observed in the same conditions in man. The mice are submitted to different treatment regimens and assessed for resistance to IA and innate and adaptive immunity parameters. The results have shown that PTX3 induced total resistance to infection and reinfection, that it activated type I protective responses and that it considerably increased the therapeutic efficacy of the antifungal agents when administered in combination.

The present invention will now be illustrated in detail, also by means of examples and figures, in which:

FIG. 1 illustrates the effect of the administration of PTX3, AmBisome (L-AmB) or Fungizone (D-AmB) in mice with invasive aspergillosis. Lethally irradiated C3H/HeJ mice were infused with T-cell-depleted BM cells of BALB/c mice ($2 \times 10^6$) one week before intra-nasal infection with $2 \times 10^7$ *Aspergillus* conidia. The mice were treated with PTX3 or with the polyenes, at the doses and via the routes indicated, 5 days before (Pre-) or after (Post-) or concomitantly with infection (Con.), in each case repeating the administration for the next 5 days. Resistance to the infection was assessed as percentage survival. The fungal load in the lungs, brains and kidneys of the infected mice was quantified by serial plating on the Sabouraud dextrose medium of the lavages of the various organs and the results were expressed as colony forming units (CFU) (mean±SE) in samples taken from the organs indicated and performed at the time of death for the mice that died prior to infection or otherwise at 6 days after infection. The groups consisted of 6 animals.

* Indicates $P<0.05$ (treated vs. untreated mice).

Figure 2:
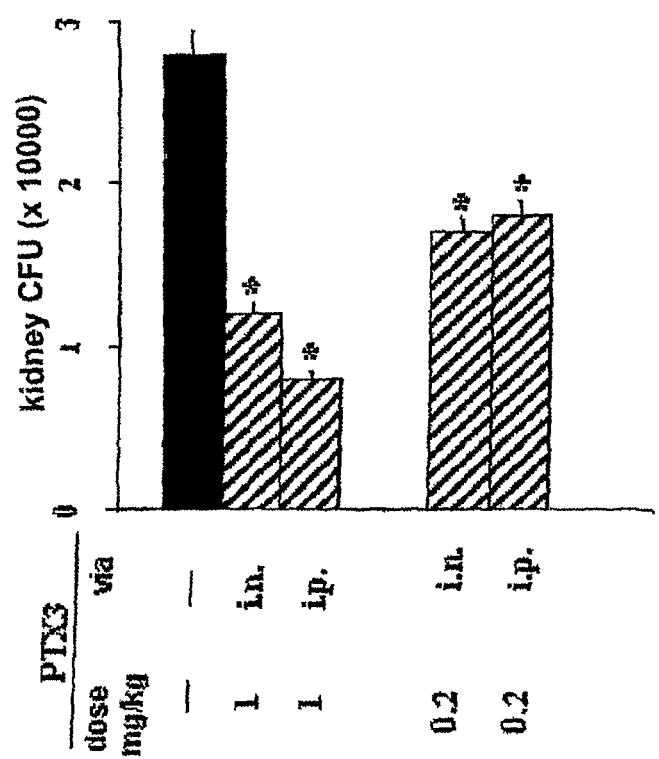

FIG. 2 illustrates the effect of the administration of PTX3 on resistance to *Aspergillus* reinfection. BM-transplanted mice, generated as described in detail in the legend to FIG. 1, were infected intranasally with $2 \times 10^7$ *Aspergillus* conidia one week after the BM transplant and treated concomitantly with PTX3 at the doses and via the administration routes indicated, starting on the day of infection and continuing for the next 5 days. Two weeks after the infection the surviving mice were reinfected intravenously with $5 \times 10^5$ *Aspergillus* conidia. The fungal growth (CFU) in the kidneys was evaluated 3 days after reinfection. * Indicates $P<0.05$ (treated vs. untreated mice).

FIG. 3 shows that PTX3 reduces the lung disease in mice with invasive aspergillosis. Periodic Schiff base sections were prepared from the lungs of the BM-transplanted mice infected with *Aspergillus* conidia either untreated (A) or treated (B) with 1 mg/kg PTX3 intraperitoneally from the day of infection and continuing for another 5 days. Numerous *Aspergillus* hyphae (arrows) infiltrate the pulmonary parenchyma, with extensive parenchymal destruction and strong signs of damage to the bronchial wall, and necrosis and poor cell recruitment are observed in the lungs of the untreated mice (3 days after infection). PTX3-treated mice present pulmonary tissue characterised by curative infiltrates of inflammatory cells with no evidence of parenchymal destruction or fungal growth (6 days after infection). Enlargement, ×100 in panels A and B; ×400 in insets.

Figure 4:
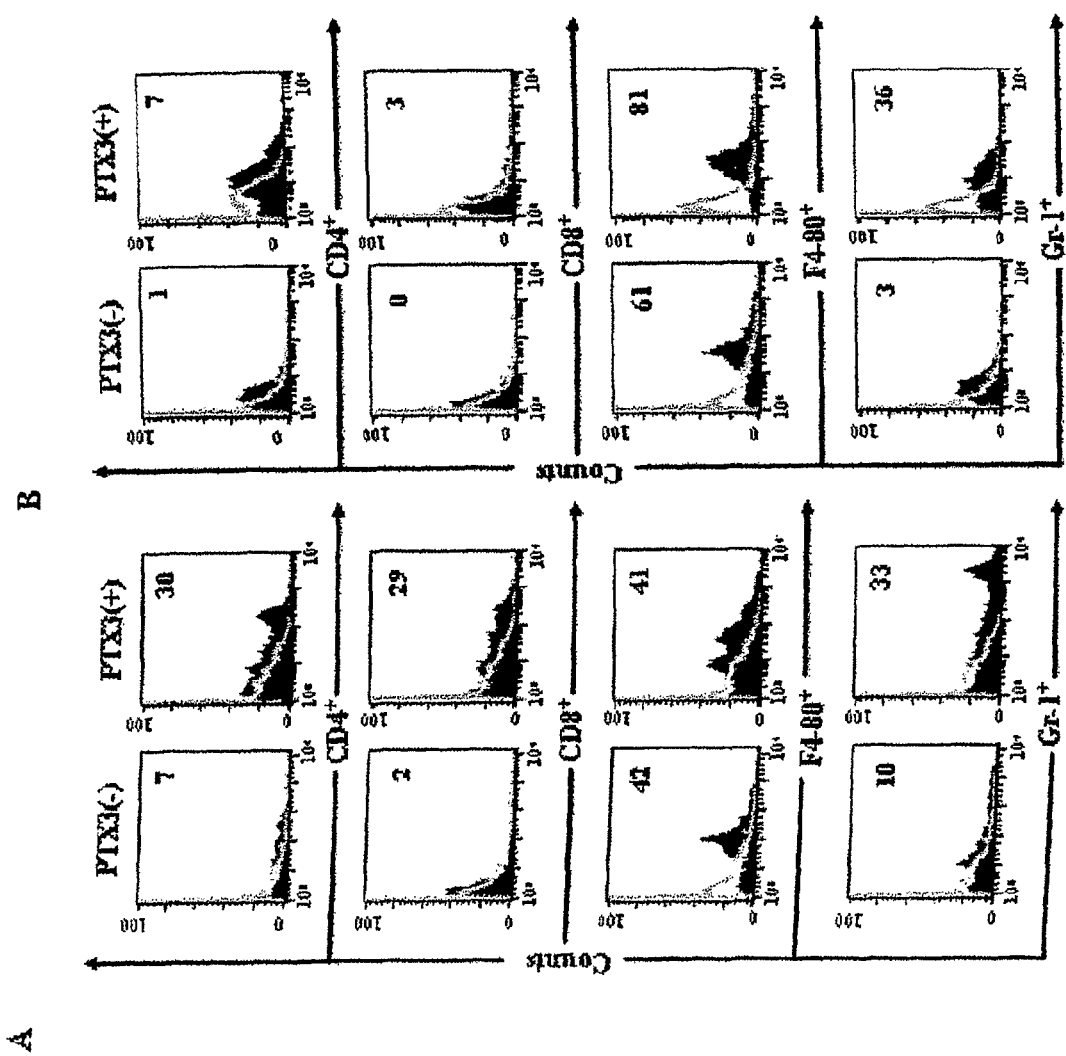

FIG. 4 shows that PTX3 accelerates cell recovery in mice with invasive aspergillosis. BM-transplanted mice, generated as described in detail in the legend to FIG. 1, were infected intranasally with $2 \times 10^7$ *Aspergillus* conidia and treated (+) or untreated (−) with 1 mg/kg PTX3 intraperitoneally from the day of infection and continuing for another 5 days. The numbers refer to the percentage of positive cells, reported by the FACS analysis in the lungs (A) and in the spleen (B), 3 or 6 days after infection.

Figure 5:
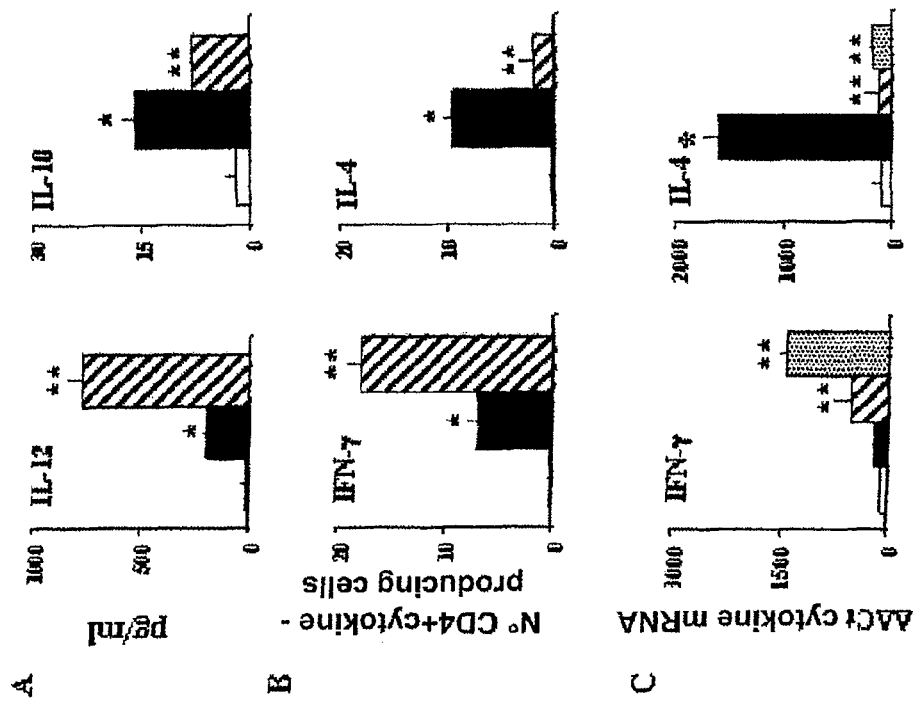

FIG. 5 shows that PTX3 induces functional recovery of the Th1 cells. BM-transplanted mice, generated as described in detail in the legend to FIG. 1, were infected intranasally with $2 \times 10^7$ *Aspergillus* conidia and treated with 1 mg/kg PTX3 intraperitoneally both before infection (oblique line bars) and from the day of infection and continuing for another 3 days (dotted bars). At 3 days after infection, IL-12 p70 and IL-10 levels were determined by specific ELISA analyses in bronchoalveolar lavage fluids (A), the number of $CD4^+$ T spleen cells producing cytokines were numbered by ELISPOT analysis (B) and the gene expression of cytokine on $CD4^+$ spleen cells was determined by real-time PCR. Bars indicate standard errors. *$P<0.05$, infected vs. non-infected mice; **$P<0.05$, PTX3-treated vs untreated mice. Non-infected mice (white bars); infected mice (black bars).

Figure 6:
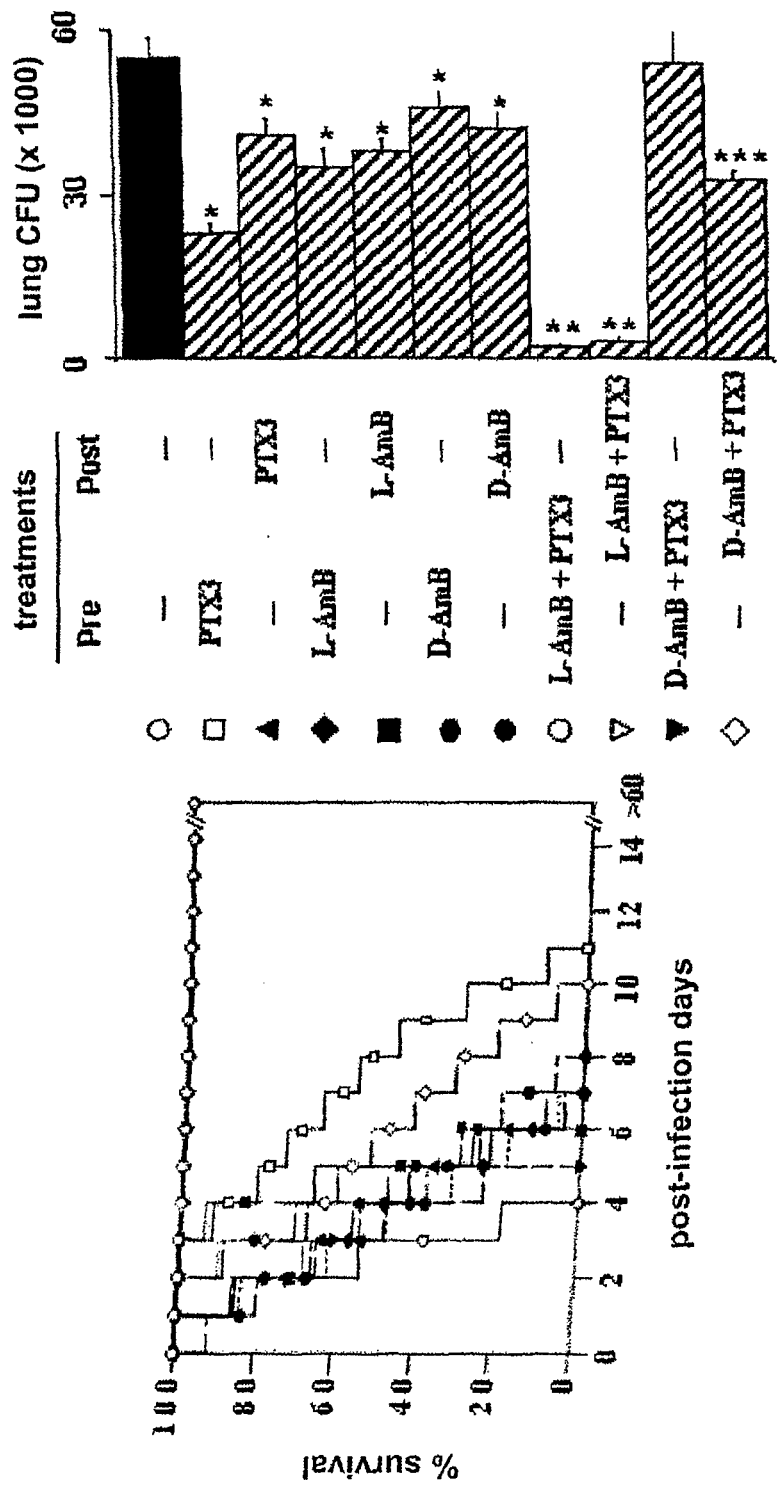

FIG. 6 shows that PTX3 increases the therapeutic efficacy of AmBisome (L-AmB) and Fungizone (D-AmB). BM-transplanted mice, generated as described in detail in the legend to FIG. 1, were infected intranasally with $2 \times 10^7$ *Aspergillus* conidia and treated intraperitoneally with each single agent alone or in combination, before (Pre-) or after (Post-) infection. The doses were: 0.04 and 0.2 mg/kg PTX3 before or after infection, respectively; 1 mg/kg AmBisome and 2 mg/kg Fungizone. Resistance to infection was evaluated as percentage survival and as CFU from the lungs, performed at the time of death for those mice that died before, or otherwise at 6 days after infection. *$P<0.05$, treated vs. untreated mice; $P<0.001$, combination treatment with PTX3+L-AmB vs each single treatment alone; *$P<0.05$, combination treatment with PTX3+D-AmB vs D-AmB alone.

Figure 7:
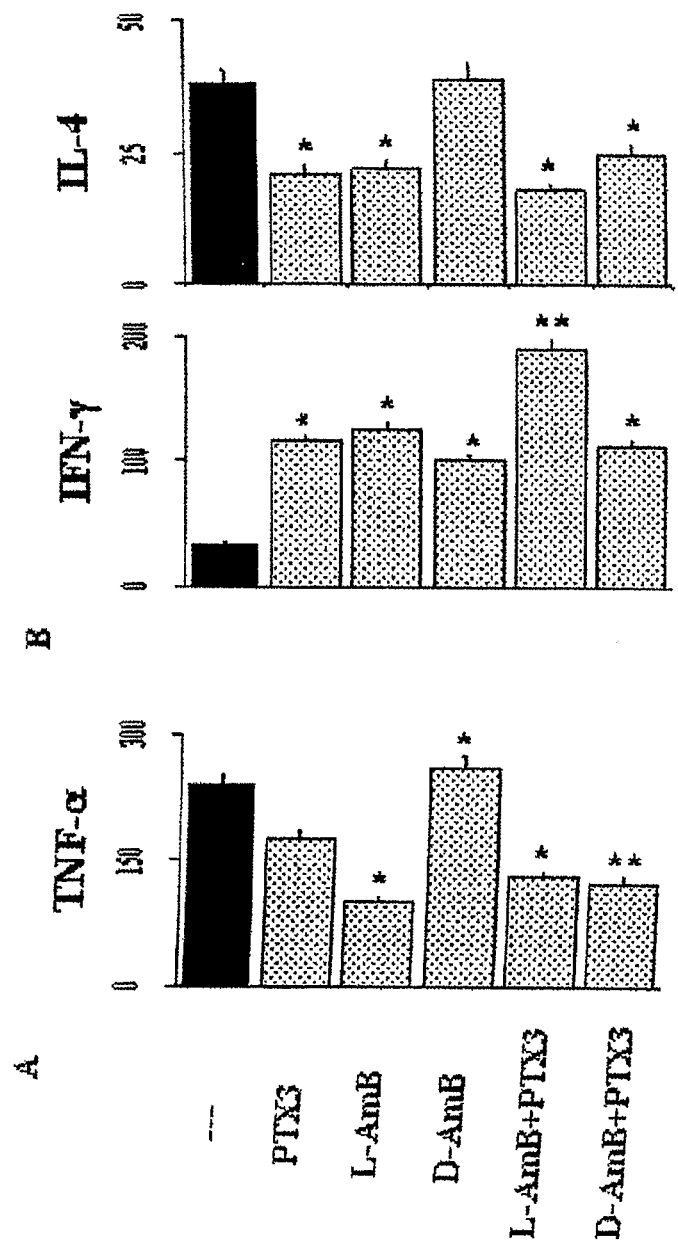

FIG. 7 shows that PTX3 reduces the production of TNF-α and increases the Th1:Th2 cytokine ratio in mice treated with the polyenes. BM-transplanted mice, generated as described in detail in the legend to FIG. 1, were infected intranasally with $2 \times 10^7$ *Aspergillus* conidia and treated intraperitoneally with each individual agent alone or in combination after infection. The dosages were as described in detail in the legend to FIG. 6. TNF-γ levels (pg/ml) were determined in bronchoaleveolar lavage fluids 3 days after infection (A) and IFN-γ and IL-4 levels (pg/ml) in the culture supernatants of the antigen-activated spleen cells (B) performed at the time of death for those mice that died before, or otherwise at 6 days after infection. Bars indicate standard errors. (−, untreated mice). *$P<0.05$ treated vs. untreated mice; $P<0.05$, combination treatment with PTX3+Fungizone (D-AmB) vs D-AmB alone; *$P<0.05$, combination treatment with PTX3+AmBisome (L-AmB) vs each single treatment alone.

MATERIALS AND METHODS

Animals.

Female BALB/c and C3H/HeJ mice aged 8-10 weeks were supplied by Charles River Breeding Laboratories (Calco, Italy). The mice were bred under specific axenic conditions. BM-transplanted mice were housed in small sterile cages (5 animals per cage) and fed with sterile feed and water. All procedures regarding the animals and their care were carried out in conformity with national and international laws and standards. All in-vivo studies were conducted in conformity with the national guidelines and with those of the Committee for the Care and Use of Animals of the University of Perugia.

BM-Transplant Model.

Bone marrow (BM) cells from BALB/c donor mice were prepared by differential agglutination with soy agglutinin. T-lymphocyte-depleted cells (less than 1% of contaminating T cells as measured by FACS analysis) were injected intravenously (i.v.) at a concentration of $\geq 4\times10^6$/mL in recipient C3H/HeJ mice exposed to the lethal dose of 9 Gy (33). Without the BM transplant, the mice died within 14 days. According to previous studies (33), more than 95% of mice survived, which shows a haematopoietic chimerism of the stable donor, as detected by the expression of MHC class I, of the donor type, in cells from the spleen.

Micro-Organism, Culture Conditions and Infection.

The *A. fumigatus* strain was supplied by a fatal case of pulmonary aspergillosis at the Institute for Infectious Diseases of the University of Perugia (13). For infection, the mice were lightly anaesthetised by means of the inhalation of ethyl ether prior to the instillation of a suspension of $2\times10^7$ conidia/20 μL saline solution, which was delivered slowly through the nostrils using a micropipette with a sterile disposable tip. This procedure was repeated for 3 consecutive days. For reinfection, the mice surviving the primary intranasal (i.n.) infection were inoculated with $5\times10^5$ of *Aspergillus* conidia i.v. The fungal load in the lungs, brain and kidneys of the infected mice was quantified by serial plating on Sabouraud dextrose medium and the results (mean±SE) were expressed as colony forming units (CFU) in samples taken from the organs indicated. For selected experiments, the fungal growth was also evaluated by chitin analysis (10). For the histological analysis, the lung was removed and immediately fixed in formalin. Sections (3 to 4 μm) of tissues embedded in paraffin were stained with the periodic acid Schiff base procedure (13, 20).

Treatments:

PTX3 (SIGMA-Tau, Pomezia, Rome, Italy) was purified by immunoaffinity chromatography from the culture supernatants of CHO cells CHO transfected with PTX3 and monitored for the absence of endotoxins (20). PTX3, amphotericin B deoxycholate (D-AmB, Fungizone, Bristol-Myers Squibb, Sermoneta, Italy) and liposomal amphotericin B (L-AmB, AmBisome, GILEAD, Milan, Italy) were diluted to the desired concentrations in sterile saline solution (PTX3) or in a 5% glucose-water solution. The treatments were carried out according to the following schedule: different doses of PTX3, amphotericin B or AmBisome, alone or in combination, were administered intraperitoneally (i.p.) or intranasally (i.n.) (PTX3 only) for 5 days before infection with *Aspergillus* (prophylactic treatment), concomitantly with infection and for 5 days after infection, or for 5 days after the last injection of conidia (therapeutic treatment). In the case of i.n. administration, the PTX3 and the conidia were administered separately. The control animals received only the diluent or sterile saline solution.

Flow Cytometry.

The phenotype of the various cell types was assessed using murine antibodies against the antigens indicated with rat antimouse antibodies conjugated with FITC from PharMingen (San Diego, Calif.). Prior to immunochemical identification, the FcR was saturated by incubation of the cells with 5% normal serum. Histotype antibodies were used as controls. The analysis was done by means of FACScan (Becton Dickinson, Mountain View, Calif.). The data obtained were evaluated as percentage of positive cells. The histograms are representative of one of four independent experiments.

Quantification of Transcripts of Cytokines by Real-Time RT-PCR.

Total RNA (5 μg, extracted from CD4$^+$ T spleen cells using the RNeasy Mini Kit (QIAGEN S.p.A., Milan, Italy)) was retrotranscribed with Sensiscript reverse transcriptase (QIAGEN) according to the manufacturer's indications. The primers for PCR were obtained from Applied Biosystems (Foster City, Calif.). The samples were subjected to 40 amplification cycles at 95° C. for 15 seconds, and then at 60° C. for 1 min using the ABI PRISM 7000 Sequence Detection System (Applied Biosystems). PCR amplification of the eukaryotic 18S rRNA housekeeping gene was done in order to allow normalisation of samples according to the manufacturer's instructions (Applied Biosystems). The controls with water were included in order to ensure specificity. All the data were examined for integrity by analysis of the amplification graph. The data normalised with RNA 18S were expressed as relative mRNA of the cytokines examined (ΔΔCt) and compared with those of naive mice (10).

Analysis of Cytokines and "Spot Enzyme-Linked Immuno-Sorbent" (ELISPOT) Analysis.

The levels of cytokines in the bronchoalveolar lavage fluids and in the supernatants of the cultures of spleen cells stimulated with *Aspergillus* (9, 10), thermally activated, were determined using the ELISA Kit (R&D Systems, Inc. Space Import-Export srl, Milan Italy). The detection limits of the analyses (pg/ml) were <16 for IL-12 p70, <32 for TNF-α, <10 for IFN-γ and <3 for IL-4 and IL-10. For the numbering of the CD4$^+$ T cells producing cytokines, ELISPOT analysis was used on purified CD4$^+$ T spleen cells (9, 10). The results were expressed as the mean number of cells producing cytokines (±SE) per $10^5$ cells, calculated using replicates of the serial cell dilutions.

Statistical Analysis.

The log-rank test was used for the analysis of the paired data of the Kaplan-Meier survival curves. Student's t-test or analysis of variance (ANOVA) and the Bonferroni test were used to determine the statistical significance of the differences in organ clearance and in the in-vitro analyses, as indicated in the figure legends. Significance was defined as P<0.05. The in-vivo groups consisted of 4-6 animals. The data reported were pooled from the 3-5 experiments, unless otherwise specified.

Results

As previously demonstrated, the exogenous administration of PTX3 restored the antifungal resistance in PTX3-deficient mice with IA (20). To assess whether PTX3 may have a beneficial effect in otherwise susceptible mice, we used BM-transplanted mice whose substantial susceptibility to IA is well documented (15). The mice were subjected to treatments with different doses of PTX3 administered intranasally or intraperitoneally, before, concomitantly with or after infection. The doses were selected on the basis of preliminary experiments showing that PTX3 levels (at the dose of 0.5 mg/kg/i.n.) were high in bronchoalveolar lavage fluids for at least 24 h (from 70 to 25 ng/ml from 2 to 24 h) and that they were higher than those observed in mice with IA one day after infection (from 2 to 15 ng/ml) (20 and unpublished data). The survival parameters and fungal load in the lung and brain were then recorded and analysed in comparison with those obtained in mice treated with different doses of AmBisome or Fungizone. The results showed that PTX3 administered prophylactically (FIG. 1A) induced total resistance to IA at any of the doses assayed, as revealed by the increase in survival (≥60 days) of the majority (from 85 to 95%) of the mice treated and by the significantly reduced fungal load in the lungs and brain, particularly in the mice that received the highest dose (1 mg/kg). Similar results were obtained in mice that received PTX3 concomitantly with infection (FIG. 1B). A dose-dependent effect was detected for this administration period, in that the protective efficacy of PTX3 was lost at the dose of 0.04 mg/kg. PTX3 administered after infection increased the survival of the mice only at the higher dose, although at both doses it significantly reduced the fungal load in the lung and at the higher dose it significantly reduced the fungal load in the brain (FIG. 1C). No difference was observed between the two administration routes. Similar results were observed in mice treated with 5 mg/kg of AmBisome, in that all the mice survived the infection when treated before or after infection (FIG. 1D). Fungizone did not afford the same level of protection and an increase in survival was observed as well as a decrease in fungal load only at the highest tolerated dose (4 mg/kg) administered after infection (FIG. 1E). In addition, we evaluated the susceptibility of the cured mice, after treatment with PTX3, to *Aspergillus* re-infection and found that the treatment with PTX3 also significantly increased the resistance to reinfection, as revealed by the reduced fungal growth in the kidneys of the reinfected mice (FIG. 2). PTX3 also improved the lung pathology. Sections of lung from infected mice showed the presence of numerous *Aspergillus* hyphae that infiltrated the pulmonary parenchyma, with signs of severe damage to the bronchial wall and necrosis and poor recruitment of inflammatory cells (FIG. 3A). These characteristics were not observed in the mice treated with PTX3, the lungs of which were characterised by healing infiltrates of poly- and mononuclear inflammatory cells with no evidence of fungal growth or destruction of the bronchial wall (FIG. 3B). These data provide evidence of the therapeutic efficacy of PTX3 in the BM transplant condition where antifungal agents normally display reduced activity (16, 31).

In mice with IA, resistance to infection correlates with activation of Th1 cells that produce IFN-γ (12, 13). To assess whether PTX3 activated Th1 cell reactivity in BM-transplanted mice with IA, we evaluated cell recovery by FACS analysis, local cytokine production and the antifungal activity of the effector phagocytes. The quantitative evaluation of blood leukocytes indicated that the absolute number of circulating neutrophils increased significantly following treatment with PTX3 (data not shown). Nevertheless, since levels of neutrophils in the blood do not enable us to predict susceptibility to aspergillosis (5), the cytofluorometric analysis was performed on lung and spleen cells. The numbers of $CD4^+$ cells, $CD8^+$ cells and $Gr-1^+$ neutrophils were significantly increased in the lungs of mice treated with PTX3 (FIG. 4A). Recovery of neutrophils and, partly, of $CD4^+$ T cells was also observed in the spleens. No difference was noted in the number of $F4-80^+$ cells of the lungs or spleens with or without treatment with PTX3 (FIG. 4B). The cells and lymphocytes that recovered proved functionally active, as indicated by the production of pro-(IL-12) and anti-inflammatory (IL-10) cytokines in the pulmonary homogenates and by the frequency of $CD4^+$ Th1 (IFN-γ) and Th2 (IL-4). FIG. 5A shows that the treatment with PTX3 substantially increased IL-12 production (approximately 4-fold); however, the production of IL-10 was only halved (as compared to the untreated control), a result suggesting that PTX3 exerts a subtle control over the inflammatory process at the site of infection. Moreover, PTX3 treatment increased the frequency of $CD4^+$ Th1 cells in the spleen and reduced that of the cells producing IL-4 (FIG. 5B), a finding confirmed by evaluation of the mRNA expression levels of cytokines by means of quantitative PCR. FIG. 5C shows that both prophylactic and therapeutic treatment with PTX3 significantly increased the expression of IFN-γ and reduced that of IL-4. On assessing the level of antifungal activity of the effector phagocytes, it was found that the conidia-killing activity of the effector phagocytes was higher in the PTX3-treated mice than in the untreated mice (data not shown). Since in-vitro studies have ruled out any direct killing activity of PTX3 on the fungus (data not shown), these data qualify PTX3 as a new agent with substantial immunomodulatory activity on both innate and adaptive antifungal immunity.

All the above-mentioned findings prompted us to assess whether the immunomodulatory activity of PTX3 could be exploited to increase the therapeutic efficacy of AmBisome or Fungizone, because these agents are known to operate synergistically with antifungal effector phagocytes (40). For this purpose the BM-transplanted mice received PTX3 alone or together with the polenyes, at suboptimal doses at which neither of the agents had achieved the maximum therapeutic effect. The combined or single treatments were administered either before or after infection. The mice were monitored for survival, fungal growth and production of cytokines. It was found that whereas each single agent administered alone significantly reduced fungal growth in the lung, it did not significantly modify the survival of the mice, with the exception of PTX3 administered alone prior to infection. However, combined therapy with PTX3 and AmBisome, whether before or after infection, cured the mice of infection, as judged by the increased survival (>60 days) and the reduced fungal growth. The combined administration of PTX3 and Fungizone significantly increased the resistance to fungal infection compared to that of Fungizone alone when administered after infection (FIG. 6). Analysis of cytokines in the pulmonary homogenates and in the supernatants of cultured antigen-stimulated spleen cells demonstrated that PTX3 greatly reduced the production of TNF-α in the lungs of mice that received Fungizone, as compared to the levels observed in mice treated with the drug alone; the level of production of TNF-α as a reaction to AmBisome was lower compared to that induced by treatment with Fungizone and was not modified by treatment in combination with PTX3 (FIG. 7A). The production of IFN-γ by spleen cells was significantly increased as compared to untreated mice after each single treatment, and was further increased in the mice treated with PTX3 and AmBisome; in contrast, the production of IL-4 was greatly reduced both by the treatment with PTX3 and/or AmBisome, and by the combined treatment with PTX3 and Fungizone, albeit to a lesser extent (FIG. 7B). Therefore, PTX3 would appear to operate synergistically with AmBisome, more than with Fungizone, in reducing the pulmonary inflammatory response and in promoting Th1 antifungal reactivity.

PTX3 according to the present invention induced a curative response in mice with IA with minimal disease. Bearing in mind that PTX3 was effective when administered prophylactically and that it shows no direct activity on fungal cells, it would appear that the beneficial effect depends on its ability to activate a Th1-dependent protective resistance.

PTX3 activates at least two effector pathways against the pathogenic infectivity, namely, the classic complement activation pathway, in the C1q binding (35), and the promotion of phagocytosis through interaction with one or more as yet unidentified cell receptors (20). It is likely that internalisation of the conidia by the resident mononuclear cells may serve to limit the fungal infectivity and permit recovery of the myeloid and lymphoid cells in the lung. PTX3, however, also activates DCs through the production of IL-12 and expression of co-stimulatory molecules in response to *Aspergillus* conidia (20). Thus, the rapid onset of the production of PTX3 in DCs through members of the Toll-like receptor (TLR) family (18) implies a direct role of PTX3 in the amplification of innate resistance and in orienting adaptive immunity.

The production of IL-12 was increased and that of IL-10 reduced in the lungs of infected mice treated with PTX3, a result that indicates an inflammatory response. Nevertheless, the production of TNF-α was not increased by treatment with PTX3, which suggests that PTX3, like a number of collecting, may act as a fine regulator of the equilibrium between pro- and anti-inflammatory stimuli (42, 48).

According to the present invention, the therapeutic efficacy of AmBisome and Fungizone was evaluated in the BM transplant infection model which parallels the profound immuno-pathology witnessed in BM transplant recipients, where the susceptibility to invasive fungal infections is causally related to the development or otherwise of protective Th responses (15, 33). We found that AmBisome displayed superior activity as compared to Fungizone in mice with IA after BM transplant. Both daily prophylactic and therapeutic treatments with 5 mg/kg AmBisome cured the mice of infection and reduced the fungal load in the lung. With D-AmB, we observed only a slightly increased resistance to infection at the highest tolerated doses (e.g. 4 mg/kg) administered after infection.

It has been postulated that the toxicity of D-AmB, including fever and shivering, is the result of pro-inflammatory cytokine production by the innate immune cells, through a TLR-dependent mechanism (43). The murine macrophages and human cell lines that express TLR2, CD14 and the MyD88 adaptor protein responded to D-AmB with the release of pro-inflammatory cytokines, including TNF-α. Here we have discovered that the production of TNF-α was higher in mice treated with D-AmB than in those treated with L-AmB. However, the combined treatment with PTX3 greatly reduced the production of TNF-α induced by the treatment with Fungizone, whereas it concomitantly increased the therapeutic efficacy of the drug, as shown by the increased survival and reduced fungal load in the mice treated with the combination of PTX3 and D-AmB following infection. Combined therapy with PTX3 also increased the efficacy of the suboptimal dose of AmBisome without affecting TNF-α production levels, as compared to those observed with each single treatment. Therefore, the activity of PTX3 in co-administration with antifungal agents may depend on an effect that goes beyond the lowering of TNF-α production. In this connection, it is known that the efficacy of anti-fungal chemotherapy depends on the immune reactivity of the host (32) and that the different formulations of amphotericin B exert an additional antifungal activity in combination with the effector phagocytes against *A. fumigatus* (40). It has also been reported that PTX3 increases phagocytosis and the killing activity of the effector phagocytes against *Aspergillus* conidia (20).

REFERENCES

1. Adler-Moore, J., and R. T. Profitt. 1993. Development, characterization, efficacy, and mode of action of AmBisome, a unilamellar formulation of amphotericin B. J. Liposome Res. 3:429-450.
2. Adle-Moore, J., and R. T. Proffitt. 2002. AmBisome: liposomal formulation, structure, mechanism of action and preclinical experience. J Antimicrob. Chemother. 49:21-30.
3. Babbin, B. A., J. N. Greene, R. Vega, S. Iravani, N. N. Ku, and R. L. Sandin. 2000. Pathologic manifestations of invasive pulmonary aspergillosis in cancer patients: the many faces of *aspergillus*. Cancer Control 7:566-571.
4. Bennett, J. E., W. E. Dismukes, R. J. Duma, G. Medoff, M. A. Sande, H. Gallis, J. Leonard, B. T. Fields, M. Bradshaw, H. Haywood, Z. A. McGee, T. R. Cate, C. G. Cobbs, J. F. Warner, and D. W. Alling. 1979. A comparison of amphotericin B alone and combined with flucytosine in the treatment of cryptoccal meningitis. N. Engl. J. Med. 301:126-131.
5. BitMansour, A., S. M. Burns, D. Traver, K. Akashi, C. H. Contag, I. L. Weissman, and J. M. Brown. 2002. Myeloid progenitors protect against aspergillosis and *Pseudomonas aeruginosa* infection following hematopoietic stem cell transplantation. Blood 100:4660-4667.
6. BitMansour, A., and J. M. Y. Brown. 2002. Prophylactic administration of liposomal amphotericin B is superior to treatment in a murine model of invasive aspergillosis after hematopoietic cell transplantation. J. Infect. Dis. 186:134-134.
7. Bottazzi, B., V. Vouret-Craviari, A. Bastone, L. De Gioia, C. Matteucci, G. Peri, F. Spreafico, M. Pausa, C. D'Ettorre, E. Gianazza, A. Tagliabue, M. Salmona, F. Tedesco, M. Introna, and A. Mantovani. 1997. Multimer formation and ligand recognition by the long pentraxin PTX3. Similarities and differences with the short pentraxins C-reactive protein and serum amyloid P component. J. Biol. Chem. 272:32817-32823.
8. Bozza, S., R. Gaziano, G. B. Lipford, C. Montagnoli, A. Bacci, P. Di Francesco, V. P. Kurup, H. Wagner, and L. Romani. 2002. Vaccination of mice against invasive aspergillosis with recombinant *Aspergillus* proteins and CpG oligodeoxynucleotides as adjuvants. Microbes Infect. 4:1281-1290.
9. Bozza, S., R. Gaziano, A. Spreca, A. Bacci, C. Montagnoli, P. Di Francesco, and L. Romani. 2002. Dendritic cells transport conidia and hyphae of *Aspergillus fumigatus* from the airways to the draining lymph nodes and initiate disparate Th responses to the fungus. J. Immunol. 168:1362-1371.
10. Bozza, S., K. Perruccio, C. Montagnoli, R. Gaziano, S. Bellocchio, E. Burchielli, G. Nkwanyuo, L. Pitzurra, A. Velardi, and L. Romani. 2003. A dendritic cell vaccine against invasive aspergillosis in allogeneic hematopoietic transplantation. Blood 102:3807-3814.
11. Breviario, F., E. M. d'Aniello, J. Golay, G. Peri, B. Bottazzi, A. Bairoch, S. Saccone, R. Marzella, V. Predazzi, M. Rocchi, G. Della Valle, E. Dejana, A. Mantovani, and M. Introna. 1992. Interleukin-1-inducible genes in endothelial cells. Cloning of a new gene related to C-reactive protein and serum amyloid P component. J. Biol. Chem. 267:22190-22197.
12. Cenci, E., S. Perito, K. H. Enssle, P. Mosci, J. P. Latge, L. Romani, and F. Bistoni. 1997. Th1 and Th2 cytokines in mice with invasive aspergillosis. Infect. Immun. 65:564-570.

13. Cenci, E., A. Mencacci, C. Fe d'Ostiani, G. Del Sero, P. Mosci, C. Montagnoli, A. Bacci, and L. Romani. 1998. Cytokine- and T helper-dependent lung mucosal immunity in mice with invasive pulmonary aspergillosis. J. Infect. Dis. 178:1750-60.

14. Cenci, E., A. Mencacci, A. Bacci, F. Bistoni, V. P. Kurup, and L. Romani. 2000. T cell vaccination in mice with invasive pulmonary aspergillosis. J. Immunol. 165:381-388.

15. Cenci, E., A. Mencacci, A. Spreca, C. Montagnoli, A. Bacci, K. Perruccio, A. Velardi, W. Magliani, S. Conti, L. Polonelli, and L. Romani. 2002. Protection of killer anti-idiotypic antibodies against early invasive aspergillosis in a murine model of allogeneic T-cell depleted bone marrow transplantation. Infect. Immun. 70:2375-2382.

16. Denning, D. W. 1998. Invasive aspergillosis. Clin. Infect. Dis. 26:781-803.

17. Denning, D. W., S. E. Follansbee, M. Scolaro, S. Norris, H. Edelstein, and D. A. Stevens. 1991. Pulmonary aspergillosis in the acquired immunodeficiency syndrome. N. Engl. J. Med. 324:654-662.

18. Doni, A., G. Peri, M. Chieppa, P. Allavena, F. Pasqualini, L. Vago, L. Romani, C. Garlanda, and A. Mantovani. 2003. Production of the soluble pattern recognition receptor PTX3 by myeloid, but not plasmacytoid, dendritic cells. Eur. J. Immunol. 33:2886-2893.

19. Fazzini, F., G. Peri, A. Doni, G. Dell'Antonio, E. Dal Cin, E. Bozzolo, F. D'Auria, L. Praderio, G. Ciboddo, M. G. Sabbadini, A. A. Manfredi, A. Mantovani, and P. R. Querini. 2001. PTX3 in small-vessel vasculitides: an independent indicator of disease activity produced at sites of inflammation. Arthritis Rheum. 44:2841-2850.

20. Garlanda, C., E. Hirsch, S. Bozza, A. Palustri, M. De Acetis, R. Nota, A. Maccagno, F. Riva, B. Bottazzi, G. Peri, A. Doni, L. Vago, M. Botto, R. De Santis, P. Carminati, G. Siracusa, F. Altruda, A. Vecchi, L. Romani, and A. Mantovani. 2002. Non-redundant role of the long pentraxin PTX3 in anti-fungal innate immune response. Nature 420:182-186.

21. Gewurz, H., X. H. Zhang, and T. F. Lint. 1995. Structure and function of the pentraxins. Curr. Opin. Immunol. 7:54-64.

22. Grazziutti, M., D. Przepiorka, J. H. Rex, I. Braunschweig, S. Vadhan-Raj, and C. A. Savary. 2001. Dendritic cell-mediated stimulation of the in vitro lymphocyte response to *Aspergillus*. Bone Marrow Transplant. 27:647-652.

23. Hebart, H., C. Bollinger, P. Fisch, J. Sarfati, C. Meisner, M. Bauer, J. Loeffler, M. Monod, J. Latge, and H. Einsele. 2002. Analysis of T-cell responses to *Aspergillus fumigatus* antigens in healthy individuals and patients with hematological malignancies. Blood 100:4521-4527.

24. Herbrecht, R., D. W. Denning, T. F. Patterson, J. E. Bennett, R. E. Greene, J. W. Oestmann, W. V. Kern, K. A. Marr, P. Ribaud, O. Lortholary, R. Sylvester, R. H. Rubin, J. R. Wingard, P. Stark, C. Durand, D. Caillot, E. Thiel, P. H. Chandrasekar, M. R. Hodges, H. T. Schlamm, P. F. Troke, B. de Pauw, and Invasive Fungal Infections Group of the European Organisation for Research and Treatment of Cancer and the Global *Aspergillus* Study Group. 2002. Voriconazole versus amphotericin B for primary therapy of invasive aspergillosis. N. Engl. J. Med. 347:408-415.

25. Hiemenz, J. W., and T. J. Walsh. 1996. Lipid formulation of amphotericin B: recent progress and future directions. Clin. Infect. Dis. 22:5133-5144.

26. Ito, J., and J. Lyons. 2002. Vaccination of corticosteroid immunosuppressed mice against invasive pulmonary aspergillosis. J. Infect. Dis. 186:869-871.

27. Latge, J. P. 1999. *Aspergillus fumigatus* and aspergillosis. Clin. Microbiol. Rev. 12:310-350.

28. McCormack, F. X., and J. A. Whitsett. 2002. The pulmonary collectins, SP-A and SP-D, orchestrate innate immunity in the lung. J. Clin. Invest. 109:707-712.

29. Madan, T., U. Kishore, M. Singh, P. Strong, E. M. Hussain, K. B. M. Reid, and P. U. Sarma. 2001. Protective role of lung surfactant protein D in a murine model of invasive pulmonary aspergillosis. Infect. Immun. 69:2728-2731.

30. Marr, K. A., R. A. Carter, M. Boeckh, P. Martin, and L. Corey. 2002. Invasive aspergillosis in allogeneic stem cell transplant recipients: changes in epidemiology and risk factors. Blood 100:4358-4366.

31. Marr, K. A. 2003. New approaches to invasive fungal infections. Curr. Opin. Hematol. 10:445-450.

32. Mencacci, A., E. Cenci, A. Bacci, F. Bistoni, and L. Romani. 2000. Host immune reactivity determines the efficacy of combination immunotherapy and antifungal chemotherapy in candidiasis. J. Infect. Dis. 181:686-694.

33. Mencacci, A., K. Perruccio, A. Bacci, E. Cenci, R. Benedetti, M. F. Martelli, F. Bistoni, R. Coffman, A. Velardi, and L. Romani. 2001. Defective antifungal T-helper 1 (Th1) immunity in a murine model of allogeneic T-cell-depleted bone marrow transplantation and its restoration by treatment with TH2 cytokine antagonists. Blood 97:1483-1490.

34. Muller, B., G. Peri, A. Doni, V. Torri, R. Landmann, B. Bottazzi, and A. Mantovani. 2001. Circulating levels of the long pentraxin PTX3 correlate with severity of infection in critically ill patients. Crit. Care Med. 29:1404-1407.

35. Nauta, A. J., B. Bottazzi, A. Mantovani, G. Salvatori, U. Kishore, W. J. Schwaeble, A. R. Gingras, S. Tzima, F. Vivanco, J. Egido, O. Tijsma, E. C. Hack, M. R. Daha, and A. Roos. 2003. Biochemical and functional characterization of the interaction between pentraxin 3 and C1q. Eur. J. Immunol. 33:465-473.

36. Patterson, T. F., W. R. Kirkpatrick, M. White, J. W. Hiemenz, J. R. Wingard, B. Dupont, M. G. Rinaldi, D. A. Stevens, and J. R. Graybill. 2000. Invasive aspergillosis. Disease spectrum, treatment practices, and outcomes. Medicine 79:250-260.

37. Peri, G., M. Introna, D. Corradi, G. Iacuitti, S. Signorini, F. Avanzini, F. Pizzetti, A. P. Maggioni, T. Moccetti, M. Metra, L. D. Cas, P. Ghezzi, J. D. Sipe, G. Re, G. Olivetti, A. Mantovani, and R. Latini. 2000. PTX3, A prototypical long pentraxin, is an early indicator of acute myocardial infarction in humans. Circulation 102:636-641.

38. Polentarutti, N., G. Picardi, A. Basile, S. Cenzuales, A. Rivolta, C. Matteucci, G. Peri, A. Mantovani, and M. Introna. 1998. Interferon-gamma inhibits expression of the long pentraxin PTX3 in human monocytes. Eur. J. Immunol. 28:496-501.

39. Roilides, E., H. Katsifa, and T. J. Walsh. 1998. Pulmonary host defences against *Aspergillus fumigatus*. Res. Immunol. 149:454-465.

40. Roilides, E., C. A. Lyman, J. Filioti, O. Akpogheneta, T. Sein, C. G. Lamaignere, R. Petraitiene, and T. J. Walsh. 2002. Amphotericin B formulations exert additive antifungal activity in combination with pulmonary alveolar macrophages and polymorphonuclear leukocytes against *Aspergillus fumigatus*. Antimicrob. Agents Chemother. 46:1974-1976.

41. Rolph, M. S., S. Zimmer, B. Bottazzi, C. Garlanda, A. Mantovani, and G. K. Hansson. 2002. Production of the long pentraxin PTX3 in advanced atherosclerotic plaques. Arterioscler. Thromb. Vasc. Biol. 22:e10-14.

42. Sato, M., H. Sano, D. Iwaki, K. Kudo, M. Konishi, H. Takahashi, T. Takahashi, H. Imaizumi, Y. Asai, and Y.

Kuroki. 2003. Direct binding of Toll-like receptor 2 to zymosan, and zymosan-induced NF-kappa B activation and TNF-alpha secretion are down-regulated by lung collectin surfactant protein A. J. Immunol. 171:417-425.

43. Sau, K., S. S. Mambula, E. Latz, P. Henneke, D. T. Golenbock, and S. M. Levitz. 2003. The antifungal drug amphotericin B promotes inflammatory cytokine release by a Toll-like receptor- and CD14-dependent mechanism. J. Biol. Chem. 278:37561-37568.
44. Schneemann, M., and A. Schaffner. 1999 Host defence mechanism in *Aspergillus fumigatus* infections. Contrib. Microbiol. 2:57-68.
45. Steinbach, W. J., and D. A. Stevens. 2003. Review of newer antifungal and immunomodulatory strategies for invasive aspergillosis. Clin. Infect. Dis. 37(Suppl 3):S157-S187.
46. Steinbach, W. J., D. A. Stevens, and D. W. Denning. 2003. Combination and sequential antifungal therapy for invasive aspergillosis: review of published in vitro and in vivo interactions and 6281 clinical cases from 1966 to 2001. Clin. Infect. Dis. 37(Suppl 3):S188-224.
47. Wingard, J. R. 1999. Fungal infections after bone marrow transplant. Biol. Blood Marrow Transplant. 5:55-68.
48. Yang, S., C. Milla, A. Panoskaltsis-Mortari, S. Hawgood, B. R. Blazar, and I. Y. Haddad. 2002. Surfactant protein A decreases lung injury and mortality after murine marrow transplantation. Am. J. Respir. Cell Mol. Biol. 27:297-305.

The invention claimed is:

1. Method for the therapeutic treatment of pulmonary aspergillosis comprising administering effective doses of pentraxin PTX3 and amphotericin B in a liposomal formulation to a subject in need thereof.

* * * * *